(12) United States Patent
Richter et al.

(10) Patent No.: US 10,595,980 B2
(45) Date of Patent: Mar. 24, 2020

(54) TEMPORARY VALVE AND VALVE-FILTER

(71) Applicant: VALVE MEDICAL LTD., Tel Aviv (IL)

(72) Inventors: Yoram Richter, Ramat Hasharon (IL); Ety Weisz, Tel Aviv (IL); Boaz Schwarz, Bat-Yam (IL)

(73) Assignee: Valve Medical Ltd., Tel Aviv (IL)

( * ) Notice: Subject to any disclaimer, the term of this patent is extended or adjusted under 35 U.S.C. 154(b) by 360 days.

(21) Appl. No.: 14/207,844

(22) Filed: Mar. 13, 2014

(65) Prior Publication Data
US 2014/0277096 A1 Sep. 18, 2014

Related U.S. Application Data

(60) Provisional application No. 61/784,742, filed on Mar. 14, 2013.

(51) Int. Cl.
*A61F 2/01* (2006.01)
*A61B 17/12* (2006.01)
(Continued)

(52) U.S. Cl.
CPC .......... *A61F 2/013* (2013.01); *A61B 17/1204* (2013.01); *A61B 17/12109* (2013.01);
(Continued)

(58) Field of Classification Search
CPC .......... A61F 2/013; A61F 2/01; A61F 2/2427; A61F 2/243; A61F 2/2436; A61F 2/2439;
(Continued)

(56) References Cited

U.S. PATENT DOCUMENTS 3,671,979 A 6/1972 Moulopoulos
4,009,717 A 3/1977 Allen
(Continued)

FOREIGN PATENT DOCUMENTS

GB 1 581 843 12/1980
JP 53-12198 2/1978
(Continued)

OTHER PUBLICATIONS

Notice of International Preliminary Report on Patentability for PCT Application No. PCT/IB2014/001564 dated Sep. 24, 2015, 9 pages.
(Continued)

*Primary Examiner* — Katherine H Schwiker
(74) *Attorney, Agent, or Firm* — Cadwalader, Wickersham & Taft LLP

(57) ABSTRACT

A temporary percutaneous valve-filter device having valve portions non-porous to blood and filter portions non-porous to emboli but at least in part porous to blood. In one embodiment, the device has a substantially flat valve unit and a substantially flat filter unit. In another embodiment, the device has at least one open umbrella deployed configuration. In one aspect, the device has a unitary construction with one umbrella canopy with one or more filter areas with flaps allowing unidirectional blood flow. In another aspect, the device has a valve unit and filter unit, the umbrella canopies oriented in opposite directions, and the valve unit "closes" and opens to allow blood to flow to one direction. Also provided is a temporary valve system, including a core having an inverted delivery configuration and everted deployed configuration, that may be used with or without a filter unit, and a method of deployment.

28 Claims, 11 Drawing Sheets

(51) Int. Cl.
  *A61F 2/24* (2006.01)
  *A61B 17/00* (2006.01)
(52) U.S. Cl.
  CPC .. *A61B 17/12131* (2013.01); *A61B 17/12177* (2013.01); *A61B 2017/00243* (2013.01); *A61F 2/2427* (2013.01)
(58) Field of Classification Search
  CPC .............. A61F 2/2466; A61F 2002/015; A61F 2002/011; A61F 2002/016; A61F 2002/018; A61F 2250/0059; A61F 2/95; A61F 2/962; A61F 2/966; A61F 2/97; A61F 2002/9505; A61F 2002/9511; A61F 2002/9534; A61F 2002/9665; A61F 2/2433; A61F 2/2475; A61B 17/1204; A61B 17/12109; A61B 17/12122; A61B 17/12168; A61B 17/12172; A61B 17/12177; A61B 17/12031; A61B 17/12036; A61B 2017/1205; A61B 2017/12054; A61B 2017/12059; A61B 2017/00243; A61B 2017/2212; A61B 2017/2215; A61B 2017/2217; A61B 2017/320716; A61B 17/12113; A61B 17/12118; A61B 17/12045; A61B 17/221
  USPC .......................................................... 606/200
  See application file for complete search history.

(56) References Cited

U.S. PATENT DOCUMENTS

| | | | |
|---|---|---|---|
| 4,056,854 A | | 11/1977 | Boretos et al. |
| 4,109,659 A | | 8/1978 | Sheridan |
| 5,800,525 A | * | 9/1998 | Bachinski .................. A61F 2/01 606/200 |
| 6,051,014 A | * | 4/2000 | Jang ................. A61B 17/12109 604/96.01 |
| 6,989,027 B2 | | 1/2006 | Allen et al. |
| 7,320,704 B2 | | 1/2008 | Lashinski et al. |
| 2002/0049468 A1 | * | 4/2002 | Streeter ..................... A61F 2/01 606/200 |
| 2002/0062135 A1 | * | 5/2002 | Mazzocchi ...... A61B 17/12022 606/200 |
| 2004/0225354 A1 | * | 11/2004 | Allen .................... A61F 2/2412 623/2.11 |
| 2004/0254601 A1 | * | 12/2004 | Eskuri ..................... A61F 2/013 606/200 |
| 2005/0010285 A1 | * | 1/2005 | Lambrecht ............ A61F 2/2427 623/2.18 |
| 2005/0015112 A1 | * | 1/2005 | Cohn .................... A61F 2/2412 606/200 |
| 2005/0240200 A1 | | 10/2005 | Bergheim |
| 2005/0283231 A1 | | 12/2005 | Haug et al. |
| 2007/0112374 A1 | * | 5/2007 | Paul, Jr. .................. A61F 2/013 606/200 |
| 2007/0149996 A1 | | 6/2007 | Coughlin |
| 2007/0255394 A1 | * | 11/2007 | Ryan ..................... A61F 2/2412 623/1.24 |
| 2010/0087908 A1 | * | 4/2010 | Hilaire .................... A61F 2/013 623/1.11 |
| 2011/0152760 A1 | * | 6/2011 | Parker ....................... A61F 2/95 604/96.01 |
| 2012/0089102 A1 | * | 4/2012 | Chomas .................. A61F 2/013 604/247 |
| 2012/0130468 A1 | | 5/2012 | Khosravi et al. |
| 2013/0041458 A1 | | 2/2013 | Lashinski et al. |
| 2013/0053882 A1 | * | 2/2013 | Hocking ............. A61B 17/221 606/200 |

FOREIGN PATENT DOCUMENTS

| | | |
|---|---|---|
| JP | 2006-507862 A | 3/2006 |
| JP | 2008-515463 A | 5/2008 |
| JP | 2016-510616 | 4/2016 |
| RU | 2011112428 | 10/2012 |
| SU | 1424810 | 9/1988 |
| WO | WO 00/44313 A1 | 8/2000 |
| WO | WO 2011/130093 | 10/2011 |
| WO | WO 2014/177935 A3 | 11/2014 |

OTHER PUBLICATIONS

Salizzoni et al., "Transapical off-pump removal of the native aortic valve: A proof-of-concept animal study," The Journal of Thoracic and Cardiovascular Surgery, Aug. 2009, vol. 138, No. 2: 468-73.
Russian Search Report from related Russian application No. 2017136961 dated Feb. 15, 2019, 4 pages with English translation.

* cited by examiner

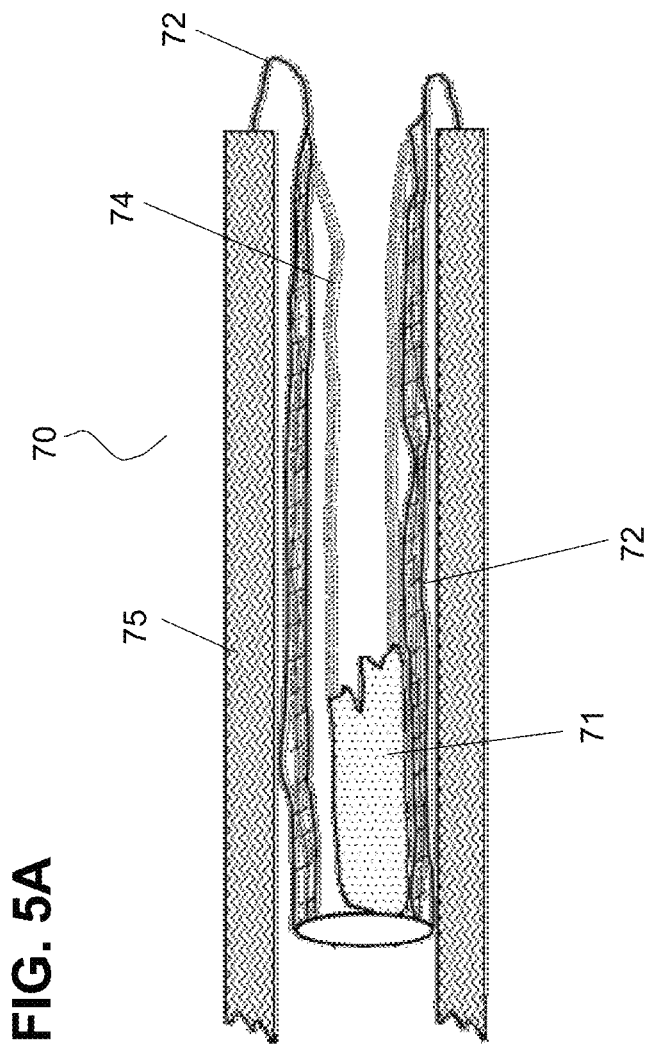

TEMPORARY VALVE AND VALVE-FILTER

FIELD OF INVENTION

The present invention relates to a temporary valve for maintaining normal blood flow and a temporary valve with embolic filter for maintaining normal blood flow while simultaneously trapping emboli during percutaneous cardiovascular procedures. The invention also relates to a system comprising such a valve or valve-filter device and a delivery device, and a method of deploying such a device.

BACKGROUND OF THE INVENTION

Valves are important structures in the human heart because they maintain blood flow in a single direction with minimal pressure loss. However, human heart valves can degenerate for a variety of reasons. A malfunctioning heart valve may be stenotic, where the leaflets of the valve do not open fully, or it may be regurgitant, where the leaflets of the valve do not close properly, or a combination of both. Valve repair and replacement procedures have thus been developed to either restore the function of the native valves or to implant a permanent prosthetic valve with or without removal of the original native valve. The standard surgical procedure involves the opening of the patient's thoracic cavity, which is highly invasive and requires cardiopulmonary bypass and prolonged recovery time.

Percutaneous valve repair and replacement procedures have been developed as cheaper and safer substitutes for the traditional open chest surgeries. Compared to traditional surgery, a percutaneous procedure is minimally invasive and it eliminates the need for cardiopulmonary bypass. In the absence of cardiopulmonary bypass, the percutaneous procedure must take place quickly to restore normal circulation, because native valve function is interrupted during the repair or the positioning and implantation of the permanent prosthetic valve. A temporary valve is a useful correlate to maintain unidirectional blood flow during the percutaneous procedure and is particularly useful in conjunction with the deployment of modular percutaneous valve devices, which require assembly prior to implantation.

Additionally, the manipulation of the delivery device, repair tools and/or valve device during a percutaneous valve repair or valve replacement procedure may dislodge tissue and/or tissue adherents such as calcium deposits and/or generate thrombi. This debris may form emboli that travel through the circulatory system and block smaller vessels, which can lead to severe complications, such as stroke, tissue ischemia or death. Consequently, it is desirable to have a filtering device to trap the emboli.

Therefore, a need exists for a single device that can simultaneously address both problems in the art, more specifically, a device that can both maintain blood flow in a single direction and contain the movement of emboli during a percutaneous valve repair or replacement procedure is highly desirable.

SUMMARY OF THE INVENTION

The present invention relates to a system and method of deploying a temporary valve having a filter to contain emboli for use during a percutaneous cardiovascular procedure. In particular, the invention provides a percutaneous prosthetic valve-filter device, a system comprising such device, and a method of percutaneously delivering and deploying the device. The system and method may be especially useful in conjunction with percutaneous heart valve repair and replacement procedures.

It is an object of the invention to provide a temporary percutaneous valve combined with an embolic protection feature—a valve-filter device, as either a unitary construction, where the valve and the embolic filter are integrated into a single unit, or as a multi-component construction, where the valve and the embolic filter functions are not integrated into a single unit, but are performed by two units that may be conjoined, overlapping or separate.

In one embodiment of the single-unit device, the valve-filter device is impermeable to blood except at blood permeable areas, for example perforations. The blood permeable areas may include filter areas which have a porosity that is permeable to blood but impermeable to emboli, and flaps that cover the filter areas. The flaps that cover the blood permeable areas may open to allow blood to flow through the blood permeable areas, for example during systole, and close to prevent backflow of the blood through the blood permeable areas, for example during diastole.

In the multi-unit temporary valve-filter device, the valve and filter functions are effected by two conjoined units, a valve unit and a filter unit. The filter unit may be made of a material permeable to blood but impermeable to emboli. The valve unit may be made of a non-porous pliable material. The valve unit and filter unit may be delivered in a closed or folded state, and after being deployed, both the valve unit and filter unit may attain an open shape. In one embodiment, the deployed valve unit and filter unit may be substantially flat, and in one aspect disk-shaped, and in another embodiment the deployed valve unit and filter unit may be umbrella-shaped. The valve unit may be supported by a frame comprising a plurality of stiff struts or a ring. In one aspect of either embodiment, the filter unit and valve unit may be separated by a distance along a longitudinal axis. In some embodiments, the valve unit is made of a material sufficiently pliable to fold inwardly, for example in one aspect of one embodiment folding inward between struts, to allow blood flow during systole, and to expand outward to the vessel wall during diastole to prevent backflow. In one embodiment where the valve unit and filter unit are substantially flat, the valve unit—positioned on the distal side of the filter unit—moves away from the filter unit during systole to permit blood flow through a filter area on the filter unit, and overlaps, and thereby covers, the filter area on the filter unit during diastole to prevent backflow. In embodiments where the valve unit and filter unit have an open umbrella shape, each umbrella canopy having a convex surface and concave surface, in one aspect of the embodiment, the convex surfaces of the two canopies may face each other and in another aspect of the embodiment, the convex surfaces of the two canopies may face away from each other.

It is also an object of the invention to provide a temporary percutaneous valve system that may be used with or without a filter unit, which provides a unique method of deploying the valve. In this embodiment the temporary valve system may include a jellyfish-shaped valve and a tubular central core attached to a sheath, for example, an introducer sheath. The valve and central core are folded in an inverted manner within the sheath in a delivery configuration and are deployed by everting the valve and central core using a pusher. The temporary valve system may be used with or without a filter element. The system is designed to accommodate the use of a catheter for delivering a permanent prosthetic valve when the temporary valve device is used in a valve replacement procedure, or for delivering a repair tool when the temporary valve device is used in a valve repair procedure.

Yet another object of the invention provides a system comprising a temporary valve-filter device mounted on a delivery device. One embodiment of the valve filter system comprises the temporary valve-filter device and a delivery device, such as a catheter, which delivers the device to the target site of a blood vessel. The valve-filter device has a delivery configuration, for example folded or closed, to minimize the delivery diameter. The valve-filter device may be delivered in or on the delivery device in a radially collapsed delivery configuration, and deployed to a radially expanded working configuration. The system is designed to accommodate the use of a catheter for delivering a permanent prosthetic valve when the valve-filter device is used in a valve replacement procedure, or for delivering a repair tool when the valve-filter device is used in a valve repair procedure. When the temporary valve is no longer needed, the valve-filter device may be removed along with the entrapped emboli.

It is a further object of the invention to provide a method of deploying a temporary percutaneous valve-filter device, comprising: introducing into a vessel, a system comprising a valve-filter device mounted on a first delivery device having a lumen, said valve-filter device designed for simultaneously regulating flow of blood and collecting emboli; said valve-filter device having a rim, a center, a closed shape in a delivery configuration, and an open shape in a deployed working configuration, said first delivery device extending through and attached to said center; advancing said valve-filter device to a target site; deploying said valve-filter device from the delivery device; and expanding radially said valve-filter device to said working configuration. The method may include deploying the valve unit and filter unit together or separately. In one embodiment, the above methods are used to deploy a valve-filter device that is a unitary device, i.e., the valve and the embolic filter functions are integrated into a single unit or structure. In another embodiment, the above methods are used to deploy a valve-filter device, where the valve and the embolic filter functions are not integrated into a single unit, but are distinct units that may be connected, conjoined, overlapping or physically separated, i.e., a multi-unit device.

In yet another embodiment, the above method further includes deploying a second delivery device, which may be extended through the valve-filter device to a vessel region distal of the deployed valve-filter for implantation of a percutaneous prosthetic valve or repair of the native valve: that is, the temporary valve-filter device may be mounted on a first delivery device having a lumen of sufficiently large internal diameter for a second delivery device to pass therethrough. In one aspect, the second delivery device is used to deliver a percutaneous valve device for permanent implantation. The method of deployment includes after said expanding step and before said collapsing step: extending said second delivery device through the center portion of said valve-filter device; deploying and implanting said percutaneous valve device; and retracting said second delivery device. In another aspect, second delivery device is used to deliver a percutaneous valve repair tool, such as, for example, a balloon used for balloon valvuloplasty. The method of deployment includes after said expanding step and before said collapsing step: extending said second delivery device through the center portion of said valve-filter device; deploying said valve repair tool and repairing a native valve; retracting said repair tool; and retracting said second delivery device.

It is a further object of the invention to provide a method of deploying a percutaneous temporary valve device. In one embodiment, the method includes providing a temporary valve device system comprising a temporary valve, a central core, lines connecting the rim of the temporary valve to the central core, and a sheath, where the temporary valve, lines and central core are folded and contained within the sheath for delivery, in an inverted configuration; pushing the central core out of the sheath using a pusher thereby inverting the central core to a deployed configuration and releasing the valve from the sheath to an open configuration. In one aspect of this embodiment, a filter unit is also deployed for use with the temporary valve device.

In yet another embodiment, the above method further include deploying a delivery device, which may be extended through the central core and valve device to a vessel region distal of the deployed valve for implantation of a percutaneous prosthetic valve or repair of the native valve: that is, the temporary valve device and central core may be mounted on a sheath having a lumen of sufficiently large internal diameter for a delivery device such as a catheter to pass therethrough. In one aspect, the delivery device is used to deliver a percutaneous valve device for permanent implantation. The method of deployment includes after said expanding step and before said collapsing step: extending said delivery device through the center portion of said valve and central core; deploying and implanting said percutaneous valve device; and retracting said delivery device. In another aspect, the delivery device is used to deliver a percutaneous valve repair tool, such as, for example, a balloon used for balloon valvuloplasty. The method of deployment includes after said expanding step and before said collapsing step: extending said second delivery device through the center portion of said valve and central core; deploying said valve repair tool and repairing a native valve; retracting said repair tool; and retracting said delivery device.

Advantages that may be achieved by the present invention include combined maintenance of blood flow and minimization of emboli in the blood stream requiring deployment of a single device. The installation of the percutaneous temporary valve-filter before commencing percutaneous vascular procedures, such as implanting a permanent percutaneous prosthetic device or repairing a native valve, may alleviate the time pressure for such further procedures by preventing wide open regurgitation of blood. In other words, the temporary valve or temporary valve-filter device of the invention permits stabilization of the system during a valve replacement or valve repair procedure. For example, when used during replacement with a modular percutaneous valve device, the temporary valve provides sufficient time to deploy and dock the valve modules into the modular frame. The embolic filter function of the temporary valve-filter of the invention minimizes the escape of emboli that may be generated during a percutaneous procedure thereby avoiding embolic blockage of the blood vessels. As such, the valve-filter device of the invention may improve the safety and outcome of percutaneous cardiovascular procedures.

BRIEF DESCRIPTION OF THE DRAWINGS

FIGS. 5A-C illustrate an embodiment of the percutaneous temporary valve system of the invention and a method of deploying the valve in cut-away views. FIG. 5A depicts the folded state; FIG. 5B depicts deployment; FIG. 5C depicts the deployed state.

DETAILED DESCRIPTION OF THE INVENTION

Figures 1, 1A:
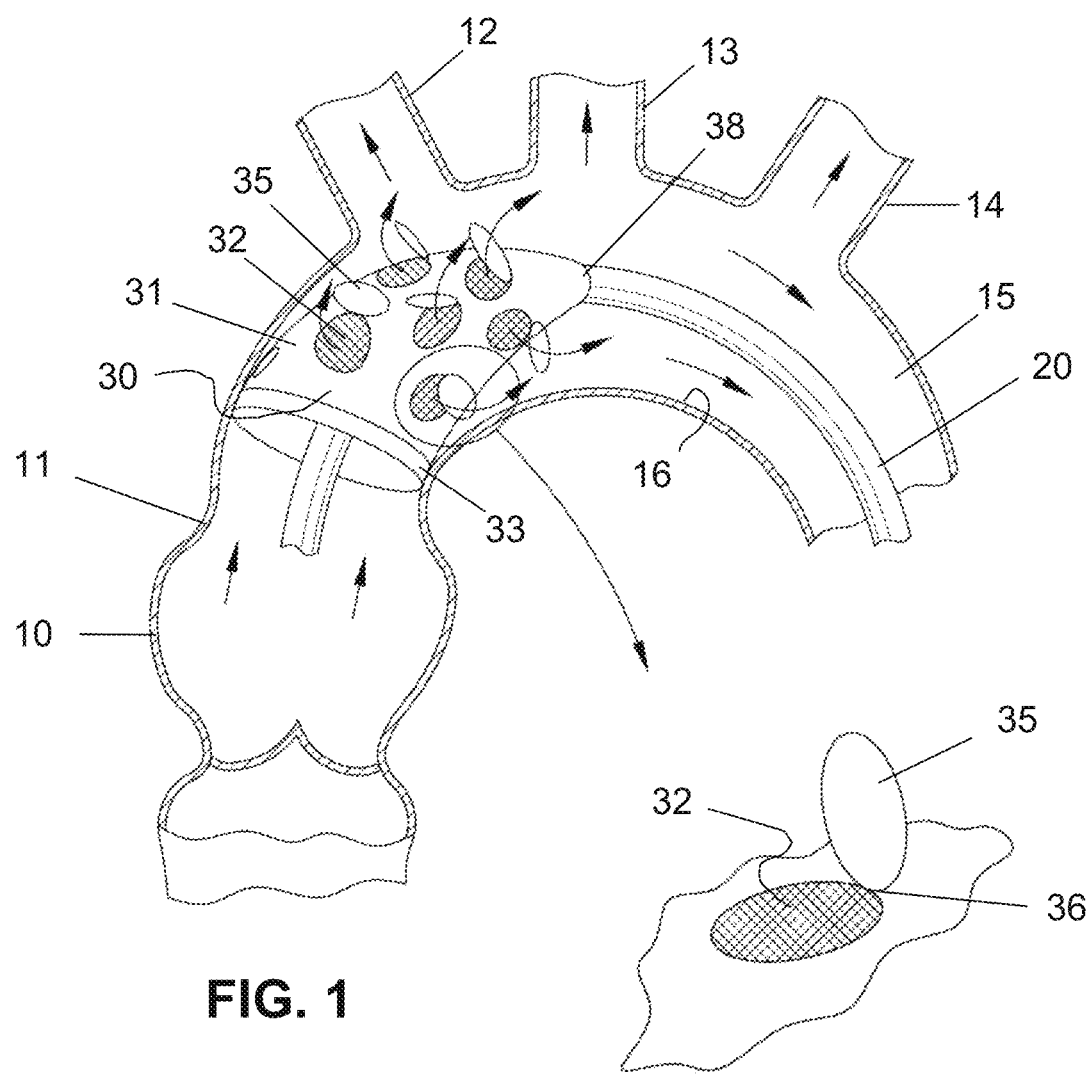
FIG. 1 illustrates an embodiment of the temporary valve-filter device having unitary construction after deployment at the target site of a blood vessel.
FIG. 1A is an enlarged view of the circled area of FIG. 1, which depicts a filter area.

The present invention provides a percutaneous temporary valve-filter device and systems and methods for deploying the valve-filter device, for example in a blood vessel. The invention also provides a percutaneous temporary valve system and a method of deploying the temporary valve. The temporary valve system may be used with or without a filter unit.

The percutaneous temporary valve-filter device may be an integrated, or unitary, device—a device comprising one unit providing both valve and filtering functions, or it may be a multi-unit device comprising a valve unit and a filter unit that are separated or conjoined. In accordance with the invention, the percutaneous temporary valve filter device may have a variety of shapes from, for example, umbrella shaped to substantially flat. A substantially flat valve filter device may be, for example, disk shaped. The portion of the device that serves as valve is not porous to blood. The portion of the device that serves as a filter is not porous to emboli but is at least in part porous to blood. A suitable pore size for the blood-porous part of the filter portion may be in a range of, for example, 10-200 microns, 50-500 microns, 80-250 microns, 80-200 microns, or 100-200 microns.

In one embodiment of the invention the valve-filter device includes a substantially flat valve unit and a substantially flat filter unit. Each of the valve unit and filter unit may be shaped, for example, like disks—a first disk and second disk. In one aspect of the embodiment, the first and second disks are adjacent to one another, for example, overlapping. In one aspect, the first and second disks are connected at a center point, which may be a location where the first and second disks are attached to a delivery device. In another aspect of the embodiment, the first disk and second disk are separated by a distance along a longitudinal axis, which may be defined by the delivery device to which the first and second disks may be attached. In one embodiment, the second disk—the filter unit—is proximal of the first disk—the valve unit, i.e., the second disk is located at a point on the delivery device distal of the first disk.

In another embodiment, the single unit valve-filter device has the shape of an open umbrella after being deployed at the target site, with a canopy having a concave surface and a convex surface. The concave surface of the umbrella canopy faces the heart, i.e., with respect to blood flow, the concave surface faces upstream. The concave shape may provide a collection field to trap and contain emboli. The valve-filter device is made from material non-porous to blood, with the exception of one or more filter areas. The filter areas comprise areas having a pore size large enough to allow blood flow but small enough to block emboli. To prevent backflow of blood during diastole, each filter area has a corresponding flap on the convex surface of the canopy, i.e., the downstream side of the device when deployed. The flaps open during systole, when the heart pumps blood to the aorta, so that blood can pass through the filter areas, and they close during diastole, between pulses to prevent backflow of blood through the filter areas. The flaps may be attached in any number of ways that are within the skill in the art, for example by a hinge on one side, by connection at the center of a membrane covering the hole, or by being an integral piece the canopy partially cut away to reveal a layer of membrane as described in more detail below.

In yet another embodiment of the invention, the valve-filter device is a multi-unit device that has a valve unit and a filter unit which are joined. Each of the valve unit and filter unit has the shape of an umbrella, each umbrella having a canopy with a concave surface and a convex surface. The valve unit and the filter unit may be comparable in size, however their canopies are oriented in opposite directions. The canopy of the deployed filter unit is oriented so that the concave surface of the canopy faces upstream, e.g., towards the heart. The filter unit canopy comprises a filter area which may include a permeable membrane or a woven structure that allows blood to flow through but blocks emboli. The rim of the filter unit canopy preferably may form an emboli-excluding seal against the vessel wall when deployed. The canopy of the deployed valve unit is oriented so that the convex surface faces upstream, at least during diastole. The canopy of the valve unit is made of pliable material and it may be supported by a plurality of stiff struts, for example three struts. Alternatively, the canopy of the valve unit may have no struts, and operate in a manner similar to a jellyfish, as described below for the temporary valve system. During diastole, the pliable canopy of the valve unit expands to an open umbrella shape to prevent backflow. During systole, the valve unit canopy folds inward, for example between the struts, to allow blood to flow through. In one aspect of this embodiment, the concave surface of the valve unit canopy and that of the filter unit face away from each other (convex-facing). In another aspect of this embodiment, the concave surface of the valve unit canopy and that of the filter unit canopy face each other (concave-facing).

The percutaneous temporary valve system includes a valve, a valve backbone—for example, a central core, a plurality of lines connecting the valve to the backbone—for example, connecting the rim of the valve to the central core, and a sheath which may constrain the central core, the valve and the plurality of lines for delivery. The central core is folded back upon itself so as to be inverted, and may be deployed by pushing with a pusher to evert the central core to its deployed configuration.

The percutaneous temporary valve preferably is flexible and jellyfish-shaped, attached by lines to the tubular central core which likewise is flexible but stiffer than the valve. The central core may serve to hold the center of the jellyfish valve in a steady proximal—i.e., upstream—position during systole and diastole, while the body of the valve opens during diastole and closes during systole, the lines restrain the body of the valve to prevent it from inverting during diastole. The central core may be a braid or a mesh, for example made of metal or fabric, or any biocompatible material that is highly flexible so that it can invert on itself. The valve and central core have an inverted delivery configuration, and are housed for delivery in a sheath, for example, an introducer sheath. The valve and central core have an everted deployed configuration, and the components may be deployed using a pusher contained within the sheath and proximal of the valve device; pushing the pusher causes the components to be everted and ejected from the sheath in which they are delivered. The percutaneous temporary valve system of the invention may be used with or without a filter unit. The percutaneous temporary valve system of the invention is particularly useful in conjunction with percutaneous valve replacements, especially with percutaneous modular valves which require assembly in situ, as described in detail in pending US published application nos. 2010/0185275 and 2011/0172784.

The aforementioned embodiments, as well as other embodiments, are discussed and explained below with reference to the accompanying drawings. Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

FIG. 1 schematically illustrates an embodiment of a single-unit percutaneous temporary valve-filter device of the invention, where the device comprises an integrated valve-filter 30 having a canopy 31 with a concave surface, a convex surface and one or more filter areas 32. Valve-filter 30 is shown in its expanded working configuration in FIG. 1, in which it has the shape of an open umbrella and the concave surface of the canopy 31 faces the heart. In one aspect of this embodiment, the rim of the canopy 31 includes a ring 33. Ring 33 may be radially compressed into a roughly round structure with a small diameter for delivery thereby maintaining valve-filter 30 in a delivery configuration. Upon placement at the target site, ring 33 may be made to fully expand so that the valve-filter 30 assumes a working configuration. Ring 33 may be made of materials commonly used for the foldable scaffold of percutaneous prosthetic devices, for example Nitinol, stainless steel, cobalt chromium, or other biocompatible materials, for example a plastic. Ring 33 may contain flex points or kink points to assist folding or radial compression. Alternatively, ring 33 may be made of shape memory material that has radially compressed configuration for delivery, and a pre-set expanded configuration. The pre-set configuration may be thermo-mechanically set to permit body temperature trigger reversion to the pre-set configuration. In one aspect, when fully expanded, the ring 33 may achieve a diameter that allows close contact with the aorta wall 16 without applying undue pressure, thereby "sealing" the rim of valve-filter 30 against aorta wall 16 so as not to allow debris to pass around valve-filter 30. In another aspect of this embodiment the canopy rim has no ring, and the canopy material itself maintains the shape of the canopy.

Canopy 31 is made of a material non-porous to blood, with the exception of a plurality of filter areas 32, discussed below. The material for canopy 31 is substantially stiff to keep valve-filter 30 in the umbrella shape, but it is also pliable enough to conform with the bending of the aortic arch and to be folded into the delivery configuration. Material for canopy 31 may be a fabric, polymer, tissue, or other material. Non-limiting examples of suitable fabrics include polyethylene terephthalate (PET), polytetrafluoroethylene (PTFE), and polypropylene. Non-limiting examples of suitable polymers include polyether block amides such as PEBAX (Arkema S.A.), silicone polycarbonate urethane, polyurethane, silicone, nylon, and PET. Non-limiting examples of suitable tissues include bovine pericardium, porcine pericardium, and comparable minimally immunogenic tissues. Canopy 31 may further contain ribs or struts (not shown) to support the umbrella shape.

Filter areas 32 are blood permeable regions of the canopy 31, i.e., they have a porosity or pore size large enough to allow blood flow but small enough to block emboli. For example, a pore size of between 10-200 microns, 50-500 microns, 80-250 microns, 80-200 microns, or 100-200 microns may be suitable. Filter areas 32 may vary in number, shape and size to achieve the most effective passage of blood. Filter areas 32 may have any geometric shape, for example, oval as depicted schematically in FIGS. 1 and 1A, or round or rectangular. The number of filter areas 32 in canopy 31 may vary depending on the embodiment. For example, the canopy 31 may have 1-30 filter areas, or 1-10 filter areas, or 1-5 filter areas, in particular, 1 or 2 or 3 filter areas. A filter area 32 may comprise a permeable membrane. Filter areas 32 may include flaps 35, hingedly attached to the canopy 31. Flaps 35 may be in the same shape as filter areas 32 or they may have a different shape. Preferably, each flap 35 has about the same or slightly bigger area as the corresponding filter area 32, so as to cover the filter area when it closes.

The filter areas 32 may be manufactured from the same material as the canopy 31, but modified to be porous. Alternatively, the filter areas may be made a material different than that of the canopy. To manufacture filter areas 32, perforations can be made in canopy 31 by a mechanical method, for example by laser drilling or hole-punching, or by chemical reaction, depending on the material of canopy 31. In one embodiment, a filter areas 32 may be a modified regions of the canopy 31 where micropores are created, and then flaps 35 are attached. In another embodiment, a blood permeable membranes may be attached to canopy 31 to cover holes in the canopy to form the filter areas 32. Permeable membrane may be attached to the canopy 31 by methods known in the art appropriate for the materials used, for example, with adhesives, by thermal bonding, or through conventional mechanical fixtures. The flaps 35 may be hingedly attached to the canopy 31. In one embodiment, the attachment point for the flap 35 may be a hinge 36 that is a physical structure made of metal or plastic. Hinges 36 together with flaps 35 may be attached to the convex surface of canopy 31 by methods within the skill in the art, for example using adhesives, by thermal bonding, or through conventional physical fixtures. In an alternative embodiment, filter areas 32 may be made by partially cutting out shapes of the material of the canopy 31, creating flaps 35 made of the canopy material, with the portion of the flap 35 material remaining attached to the canopy 31, forming the hinge 36, and permeable membrane may be attached to the canopy 31 at the filter areas 32. By "hinge" or "hingedly" is meant, for example, a jointed or flexible attachment, serving as a pivot or fulcrum, such that the flap 35 may move about a transverse axis, like a swinging door or a bivalve shell. Permeable membrane material may be attached to the concave surface of the canopy 31 to cover the cut away portion of the canopy 31 thereby forming the filter area 32.

With reference to the particular embodiment depicted in FIG. 1, canopy 31 of valve-filter 30 may include a plurality of filter areas 32. On the convex surface of the canopy 31, i.e., the downstream side of the deployed device, each filter area 32 has a corresponding flap 35 connected to the filter area 32 by a hinge 36. During systole the pulse of blood (shown in FIG. 1 by arrows) permits the flaps 35 to open allowing blood but not emboli to pass through the filter area 32. During diastole, the flaps 35 close preventing back flow of the blood through the filter areas 32, e.g., towards the heart. FIG. 1 depicts a high density of filter areas 32, however it is contemplated that 2 or 3 such filter areas 32 with hinged flaps 35, or one large filter area, may also be suitable. The flaps 35 may be made of a pliable material that is not permeable to emboli. Non-limiting examples of the material for these pliable flaps may include fabric, polymer, tissue, or other material.

FIG. 1A schematically illustrates a close-up view of one embodiment of a filter area 32 of the embodiment of FIG. 1. As noted above, each filter area 32 may include a membrane that is porous to blood but substantially blocks emboli. Non-limiting examples of suitable membrane material include materials similar to those useful for the canopy 31 but made porous, weaves, and meshes including metallic mesh. The permeable membranes may have a pore size of, for example, about 10 µm to about 2000 µm diameter, or from about 50 µm to about 500 µm diameter, or from about 80 µm to about 200 µm diameter. Each filter area 32 has a corresponding flap 35 on the convex surface of canopy 31 and flap 35 is connected to the canopy surface via a hinge 36. Flap 35 may be made of the same material as canopy 31; or it may be made of other suitable material non-porous to blood. Flap 35 opens during systole to allow blood flow through filter area 32 in the direction away from the heart, and closes during diastole to prevent blood from flowing through filter area 32 in the reverse direction. Hinge 36 may be a passive structure, located on the convex side of the canopy 31, i.e., the side facing away from the heart, or downstream along the artery. In this way, flap 35 serves the valve function of the device. Backflow of blood during diastole closes the flaps 35 thereby limiting blood flow to a direction away from the heart.

FIG. 1 further shows a catheter 20 extending through the apex 38 of canopy 31, with the distal end of the catheter extending distal of ring 33. With respect to the catheter, the term "distal" refers to the direction closer to the heart, or upstream along the artery. Catheter 20 may deliver a permanent valve or a valve repair tool to the site distal of valve-filter 30. The apex 38 of canopy 31 is preferably attached to the catheter 20. The canopy may be attached to the catheter or delivery device 20 by means known in the art, for example, by gluing or bonding, e.g., thermal bonding.

Percutaneous temporary valve-filter 30 preferably is deployed in the aorta 10 between the sinotubular junction 11 and branching point of the right brachial artery 12, which is close to the aortic valve to be replaced, as illustrated in FIG. 1, so that debris generated by the replacement or repair can be effectively caught before entering arteries in the brachial arch. Alternatively, the temporary valve-filter device may be placed between the right brachial artery 12 and the left common carotid artery 13, or between the left common carotid artery 13 and the left subclavian artery 14, or further "down-stream". The more distal the position of the device relative to the sinotubular junction 11—specifically beyond right brachial artery 12—the greater the sacrifice of function, i.e., progressively decreasing effectiveness of trapping emboli before they enter one or more arteries.

Figures 2, 2A:
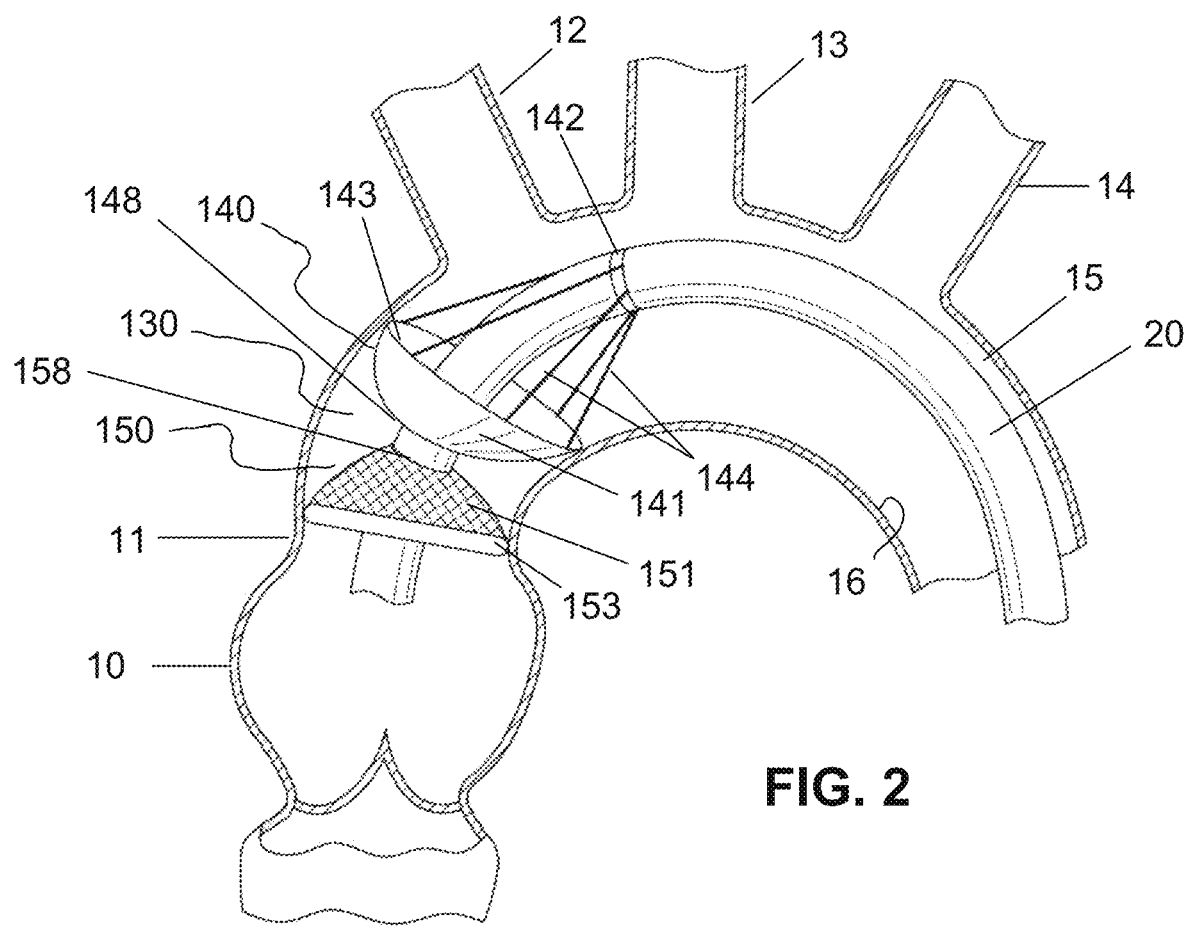
FIG. 2 illustrates a multi-unit embodiment of the valve-filter device with convex-facing valve unit and filter unit canopies, deployed at a target site of a blood vessel, and one aspect of a valve unit of this embodiment.
FIG. 2A illustrates another aspect of a valve unit of the multi-unit convex-facing embodiment of FIG. 2.
Figure 3:
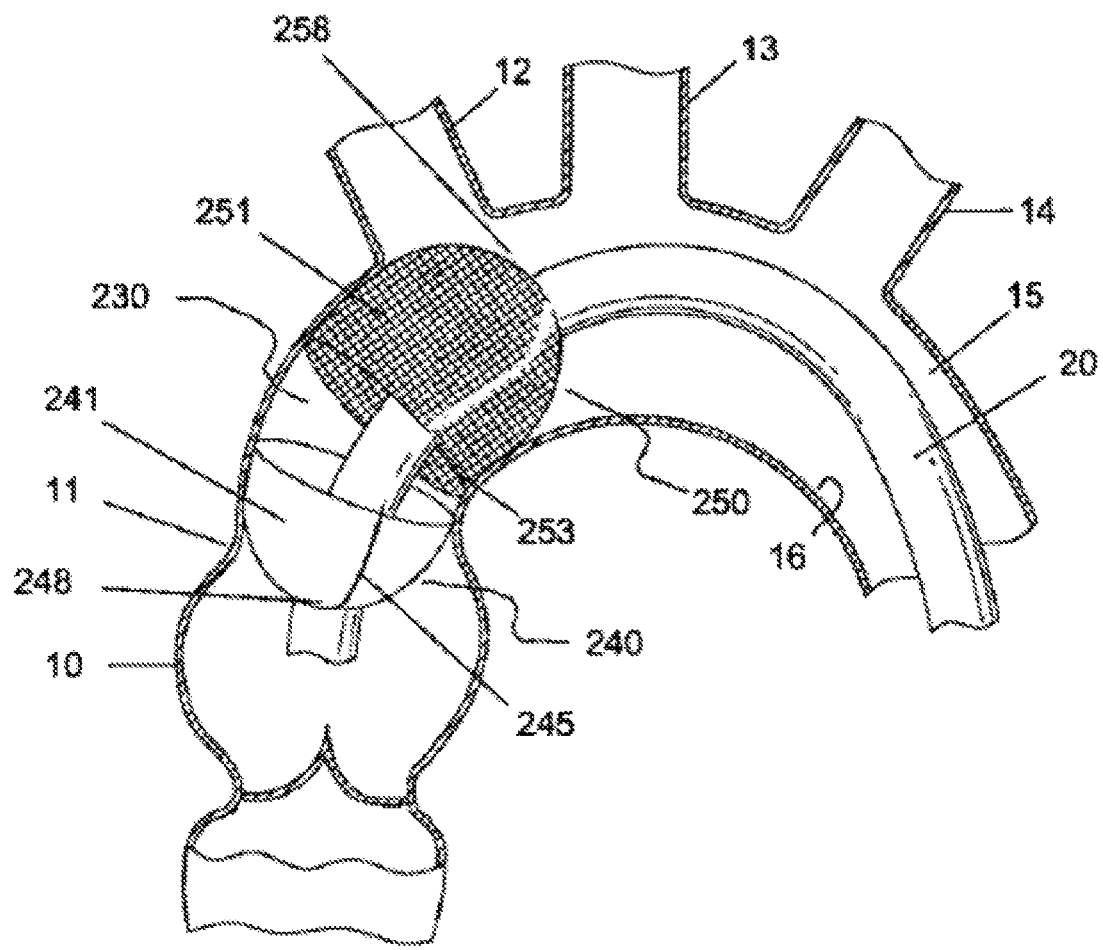
FIG. 3 illustrates a multi-unit embodiment of the valve-filter device with concave-facing valve unit and filter unit canopies, deployed at the target site of a blood vessel.

FIGS. 2, 2A, and 3 illustrate two embodiments of a multi-unit valve-filter device 130, 131 having a valve unit 140, 240 and a filter unit 150, 250, which are joined. Each valve unit 140, 240 has a valve canopy 141, 241, and each filter unit 150, 250 has a filter canopy 151, 251. When the valve-filter device 130, 230 is deployed, the valve unit 140, 240 adopts a working configuration in which the valve unit valve canopy 141, 241 has concave surface facing away from the heart and the filter unit 150, 250 adopts a working configuration in which the filter canopy 151, 251 has a concave surface facing toward the heart. The valve canopy 141, 241 is made of a pliable material that is not porous to blood, which material expands into an open umbrella shape during diastole to prevent backflow of blood towards the heart. For example, the valve canopy 141, 241 is sufficiently flexible such that during systole (not depicted), the flow of blood causes at least a portion of the valve canopy 141, 241 to bend radially inward to permit blood to flow downstream away from the heart. Non-limiting examples of materials for valve canopy 141, 241 include fabric, polymer, tissue, or other material as discussed above for canopy 31 of FIG. 1.

In one aspect of this embodiment the valve unit and filter unit are adjacent (as shown), in another aspect of this embodiment the valve unit and filter unit are separated by some distance along a longitudinal axis (not shown). In an alternative embodiment, the valve unit 140, 240 and filter unit 150, 250 are not joined and are separated by some distance along a longitudinal axis (not shown). Like the single unit embodiment of the valve-filter device 30, the multi-unit valve-filter device 130, 230 or the filter unit 150, 250 of the device, may be deployed in the aorta 15 between the sino-tubular junction 11 and branching point of the right brachial artery 12, or further downstream. When deployed, filter unit 150, 250 has the shape of an open umbrella, with the concave surface of filter canopy 151, 251 facing the heart. The rim of the filter canopy 151, 251 is a ring 153, 253. Similar to ring 33 of valve-filter 30 in FIG. 1, ring 153, 253 is radially compressed and folded when filter unit 150, 250 is in a delivery configuration, and it is expanded when filter unit 150, 250 is in a working configuration. Ring 153, 253 may be made similarly to ring 33, and the fully expanded ring 153, 253 makes close contact with aorta wall 16 without applying undue pressure, to provide a seal that limits debris from passing around filter unit 150, 250. Filter unit 150, 250 may be made of a material permeable to blood flow but impermeable to emboli. It preferably has a porosity of 80 to 200 µm; or, the pore size may be, for example, in the range of from 50 to 500 µm, or from 10 to 2000 µm. Any material with such porosity may potentially be suitable for filter unit 150, 250, provided that the material is pliable to fold, for example, the same material as the valve canopy 31, 141, 241, but modified to be porous or a material different than that of the canopy, as described above for the filter areas 32 and membranes. The porosity of the filter unit 150, 250 may also be fabricated from fibers. The fibers may be knitted, woven, or braided to achieve the desired porosity. As with the filter areas of FIGS. 1 and 1A, the filter unit of the multi-unit device may have a pore size of, for example, between 10-200 microns, 50-500 microns, 80-250 microns, 80-200 microns, or 100-200 microns.

In the embodiment illustrated in FIG. 2, the concave surfaces of the valve canopy 141 and the filter canopy 151, face away from each other (convex-facing). In one aspect of this embodiment, illustrated in FIG. 2, valve unit 140 may comprise a plurality of lines 144, which connect the rim 143 of valve canopy 141 to band 142 attached to catheter 20 proximal of the valve-filter device. Lines 144 may be wires, strings, or may be made of the same material as the valve canopy 141, and in one aspect may be a unitary construction with the valve canopy 141. In combination, lines 144 and band 142 help maintain the working configuration of valve 140. As shown in FIG. 2, in this embodiment, the pulse of blood flow during systole causes the portion of the valve canopy 141 between the points on the rim 143 where the lines 144 are connected (to bend radially inward to permit the blood to flow downstream). During diastole, backflow causes the portion of the canopy between the points on the rim 143 at which the lines 144 are connected to bend radially outward to the vessel wall so that the canopy 141 is fully open, thereby limiting blood flow downstream. In one aspect of the embodiment, the band 142 may slide back and forth along the catheter 20 moving the catheter rim via the lines 144 to allow blood to flow during systole and to prevent backflow during diastole. In another aspect of the embodiment, the band 142 may be used to control the diameter of the open valve canopy 141. Thus the device may be adjusted to the diameter of the aorta 15; in a larger aorta, the band 142 can be slid distally towards the valve canopy 141 and in a smaller aorta the band 142 could be slid proximally away from the valve canopy 141.

As illustrated in FIG. 2, a catheter 20 for delivering a permanent valve or repair tool extends through both valve unit 140 and filter unit 150, with the distal end extending to the space distal of ring 153. The apex 148 of the valve unit 140 and apex 158 of the filter unit 150, respectively, may be attached to the catheter 20.

In another aspect of this embodiment, illustrated in FIG. 2A, the valve unit 140a includes a plurality of stiff struts 145, which are connected to the apex 148 of valve unit 140a by a strut hinge 146. The stiff struts 145 help maintain the working configuration of the valve unit 140. As shown in FIG. 2A, in this embodiment, the pulse of blood flow during systole causes the portion of the valve canopy 141 between the stiff struts 145 to bend radially inward to permit the blood to flow downstream. During diastole, backflow causes the portion of the valve canopy 141 between the stiff struts 145 to bend radially outward to the vessel wall so that the valve canopy 141 is fully open, thereby limiting blood flow downstream. The strut hinges 146 allow the struts to be opened and closed in a plane perpendicular to the plane of the rim of valve canopy 141 for purposes of delivery of the valve-filter device. When valve unit 140a is in the delivery configuration, struts 145 close to constrain valve unit 140a in a small cross-section. Upon deployment, struts 145 may open through the self-expansion mechanism of hinges 146, and they open to such an angle that the tips of the struts make contact with or are substantially close to aorta wall 16. Struts 145 may be made of a stiff material such as metal or plastic. Non-limiting examples of such metals include Nitinol, shape memory alloys, metals, e.g., stainless steel or Co—Cr.

In another embodiment of the multi-unit valve-filter device 230, illustrated in FIG. 3, valve-filter device 230 includes a valve unit 240 and a filter unit 250 where the concave surfaces of the valve canopy 241 and the filter canopy 251 face toward each other. The valve unit 240 and the filter unit 250 may be constructed similarly to their counterparts in the embodiment depicted in FIGS. 2 and 2A in terms of both structure and materials. In one aspect of this embodiment, the valve filter unit 240 may include a plurality of stiff struts 245, for example three stiff struts, to form a frame for the valve-filter device. Canopies 241 and 251 may be attached to the frame. Alternatively, the valve filter unit 240 may be frameless, and constructed like the jellyfish embodiment of the temporary valve described below, for example in FIG. 5.

A first delivery system may include a sheath or mechanical constraint structure over catheter 20 and the valve-filter device for radially constraining the valve-filter device in a delivery configuration. Upon reaching the target site, the sheath may be removed and the valve-filter device deployed to its working configuration. In a further alternative, ring 33, 153 and 253 may be made of a shape memory material to permit the ring to adopt a compressed and folded delivery configuration-e.g., at a lower temperature. Cold saline solution may be infused into the blood vessel to trigger the compression and folding. A permanent valve or valve repair tool may be delivered via a second delivery device that extends through the lumen of the first delivery device.

The valve-filter system of the invention comprises a temporary valve-filter device and a first delivery device for delivering the temporary valve-filter device to the target site of the blood vessel. The valve filter device may be delivered mounted on the catheter 20 that extends through the apices of the canopy 41 or canopies 141, 151, 241, 251. The valve-filter device is preferably attached to the delivery device at all times during use. The first delivery device may further include a catheter that houses the valve-filter device within it for delivery. The valve-filter device may be deployed with pull wires and/or push rods at the target site.

As shown in FIG. 3 the concave-facing multi-unit valve-filter device 230 may also include a second delivery device, i.e., a catheter 20 for delivering a permanent valve or repair tool extending through both the apex 248 of the valve unit 240 and the apex 258 of filter unit 250, with the distal portion of the catheter 20 extending distal of apex 248 of valve unit 240. As with the valve filter-device of FIGS. 2 and 2A, during diastole, the portion of valve canopy 241 of valve unit 240 between the struts expands radially to an open umbrella shape to prevent backflow. During systole (not depicted), the same portion of valve canopy 241 folds radially inward between struts to allow blood flow through the vessel. The blood then passes through filter unit 250 so that any emboli are collected and retained in the space between valve unit 240 and filter unit 250.

Figure 4A:
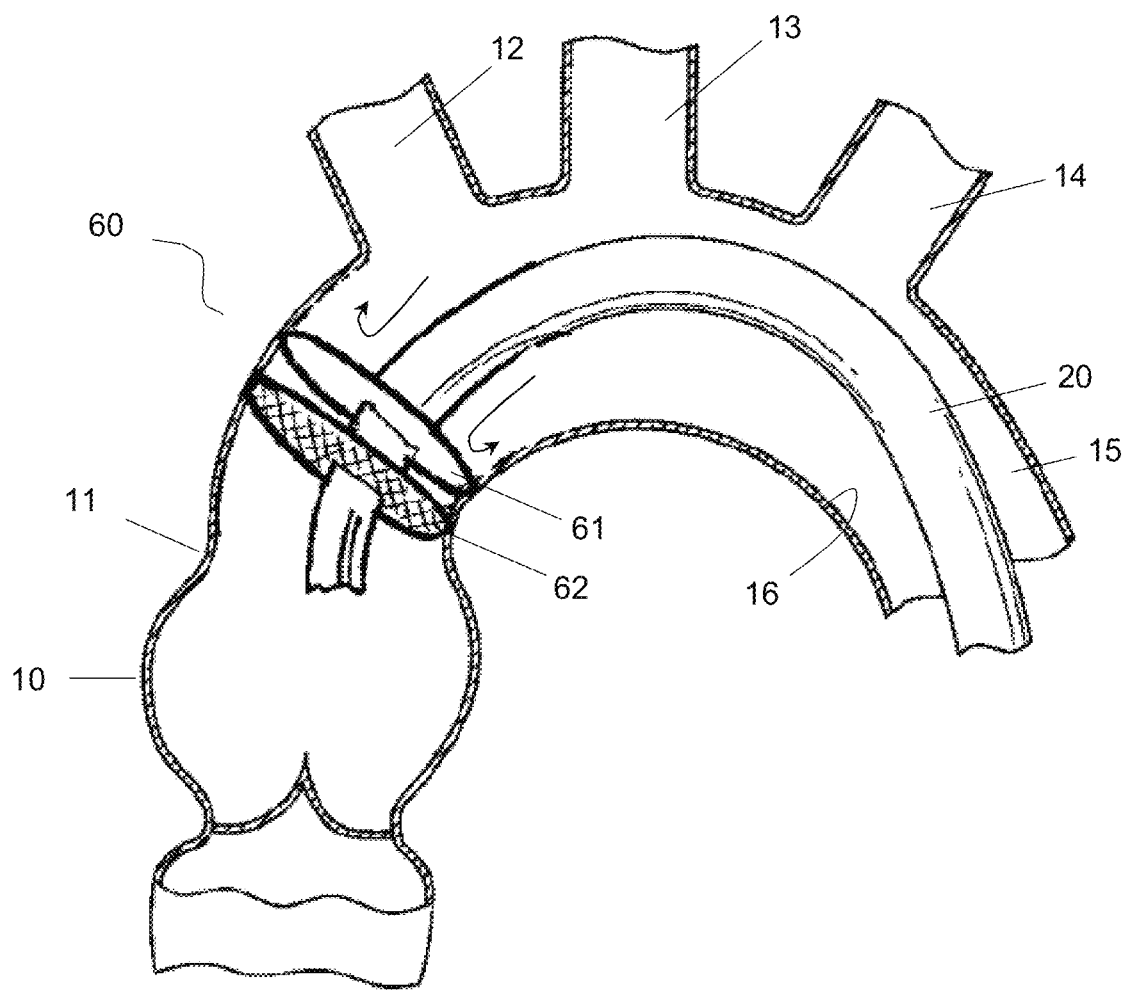
FIG. 4A illustrates one embodiment of the percutaneous substantially flat valve-filter device during diastole.
Figure 4B:
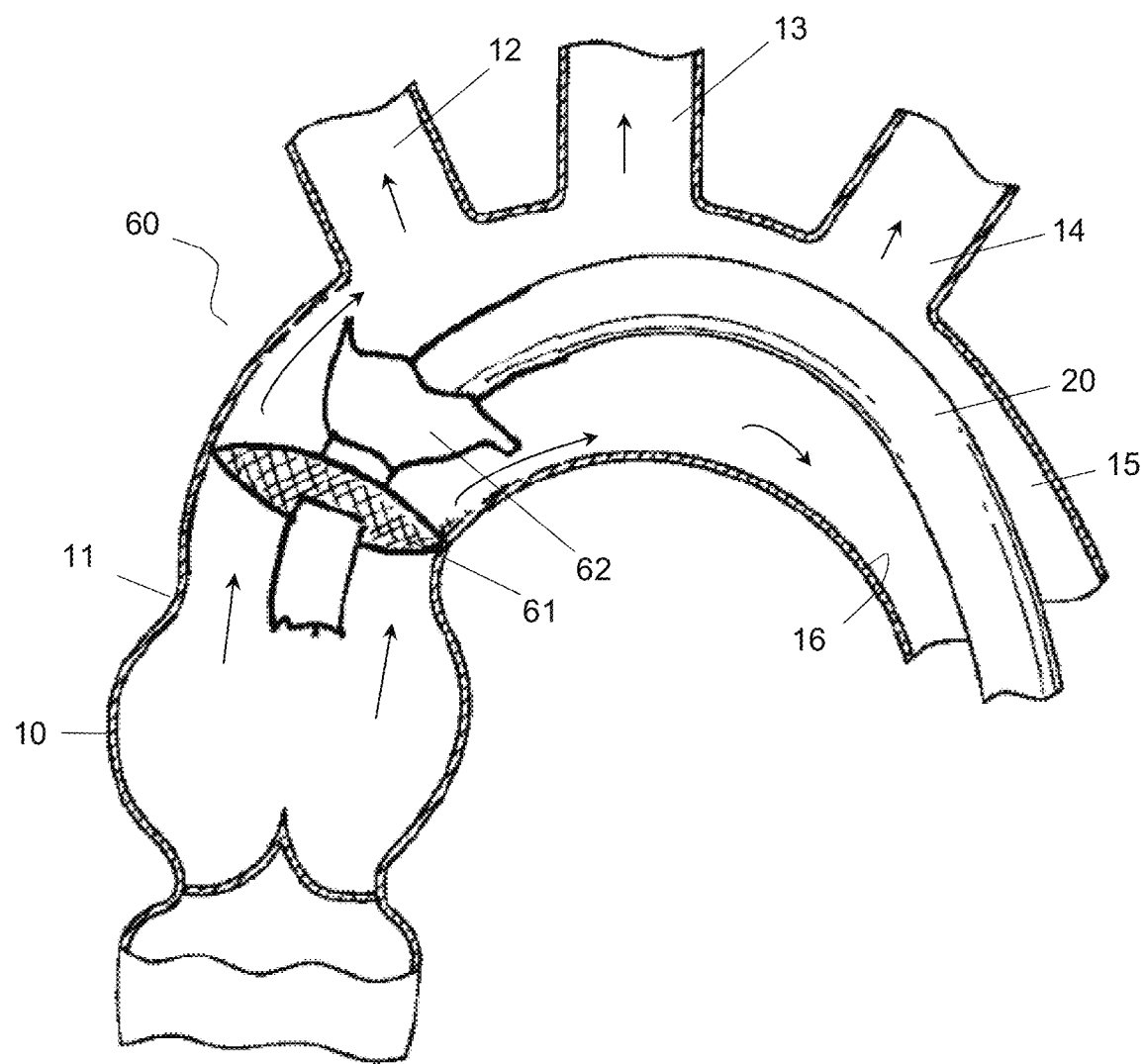
FIG. 4B illustrates the embodiment of FIG. 4A during systole.
Figure 4C:
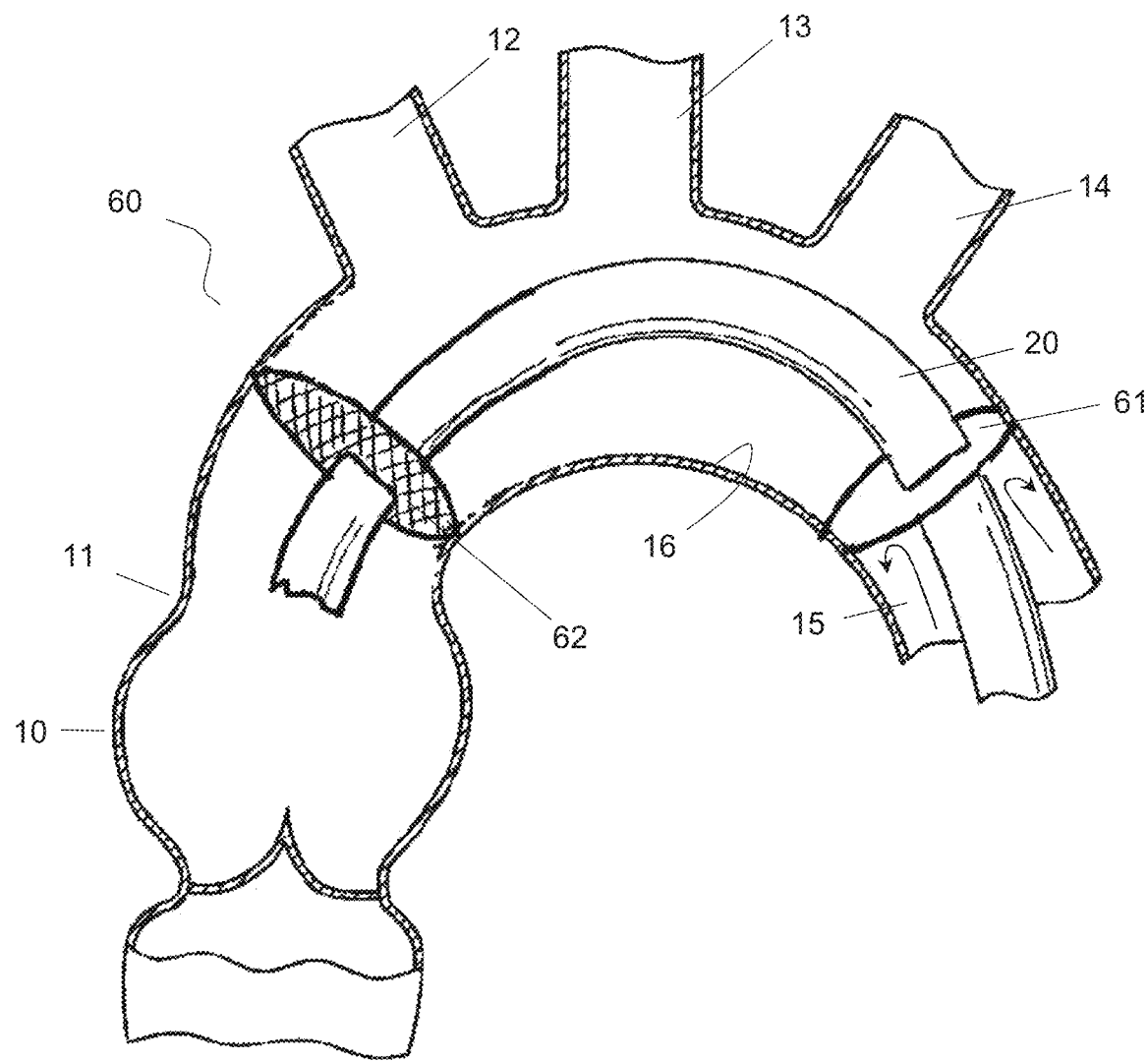
FIG. 4C illustrates another embodiment of the percutaneous substantially flat valve filter device of the invention during diastole.

In another embodiment, the valve-filter device 60 has substantially flat components, as illustrated in FIGS. 4A-4D, that may be disk-shaped, for example circular, elliptical, or the like. The device of this embodiment comprises a first substantially flat portion or disk 61, 161 and a second substantially flat portion or disk 62, 162, said first and second portions concentrically aligned. In this embodiment, the first disk 61, 161 is impermeable to blood and functions as the valve and the second disk 62, 162 is permeable to blood but impermeable to emboli and functions as an embolic filter. The second disk 62, 162 may comprise a permeable membrane, constructed of the materials described above for the embodiments of FIGS. 1-3, and having a porosity, for example, of between 10-200 microns, 50-500 microns, 80-250 microns, 80-200 microns, or 100-200 microns. The valve filter-device of FIGS. 4A-4C is designed so that blood may flow around the first disk 61, 161 which preferably is sufficiently flexible to fold downstream at least in part during systole and sufficiently stiff and elastic to regain its substantially flat configuration during diastole to minimize blood backflow. Arrows indicate direction of blood flow, and in FIGS. 4A and 4C illustrate how the valve may prevent back-flow during diastole.

In one aspect of this embodiment, the first and second disk 61, 62 may have similar diameter and lie adjacent one another as illustrated in FIG. 4A. For example, the first disk 61 may lie on top of the second disk 62, overlapping during diastole. In FIG. 4A, a small space is shown between the first and second disks 61, 62 for clarity of illustration. The first and second disks 61, 62 may be attached to each other in the center where they are connected to the delivery device 20, at points along the periphery (rims), or both. As illustrated in FIG. 4A, the first disk 61, which functions as the valve, may be fully open so that its rim contacts the vessel wall 16 during diastole to prevent backflow of blood. During systole, the first disk 61 may fold toward the center, for example toward the delivery device 20 sufficiently to allow blood flow through the vessel, as illustrated in FIG. 4B. The percutaneous valve-filter device may be placed between the sino-tubular junction 11 and branch point of the right brachial artery 12 as shown in FIGS. 4A and 4B. Alternatively, the valve filter device may be placed between the right brachial artery 12 and the left common carotid artery 13, or between the left common carotid artery 13 and the left subclavian artery 14, or further "downstream."

In another aspect of this embodiment, the first and second disk may be separated but located along a common longitudinal axis, as illustrated in FIG. 4C. To maximize filtering of emboli into the arteries, the second disk 62 having the filtering function is located between the sino-tubular junction 11 and the right brachial artery 12. However, the second disk alternatively may be placed between the right brachial artery 12 and left common carotid artery 13, or between the left common carotid artery 13 and the left subclavian artery 14.

Figure 4D:
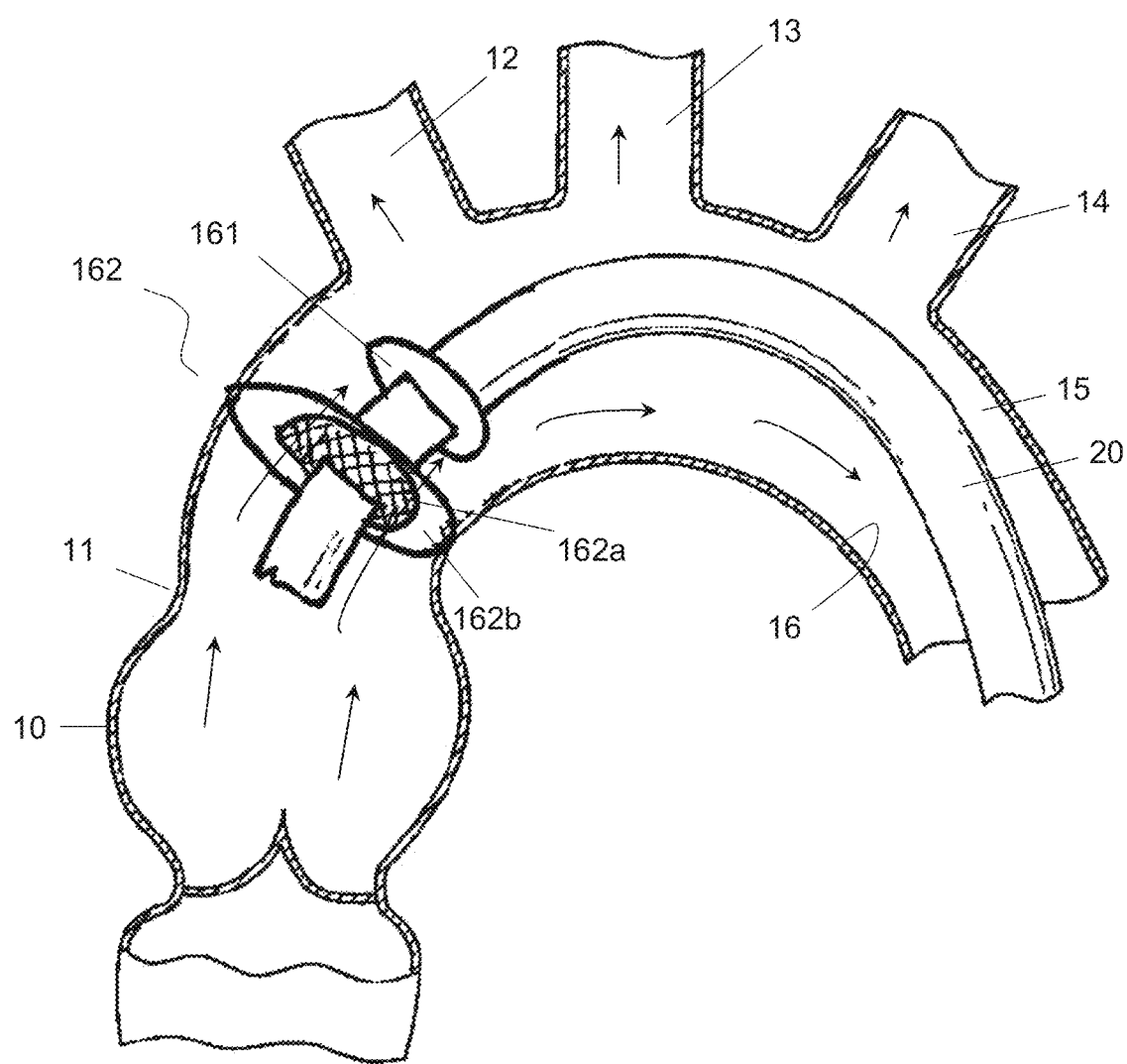
FIG. 4D illustrates another embodiment of the percutaneous substantially flat valve filter device of the invention during systole.

In yet another aspect of this embodiment, illustrated in FIG. 4D, the second disk 162 may have a radial inner portion 162*a* that is permeable to blood but impermeable to emboli and a radial outer portion 162*b* that is impermeable to blood. The first disk 161, impermeable to blood, may lie adjacent to and overlap the radial inner portion 162*a* of the second disk 162 during diastole, closing the permeable radial inner portion 162*a* to limit backflow of blood (not shown), but slide distally along the delivery device 20 to open the valve-filter device, so that the blood may flow through the radial inner portion of the second disk, as illustrated in FIG. 4D. Arrows indicate direction of blood flow. Preferably, the valve-filter device of this aspect of the embodiment includes a "stop" (not shown) on the delivery device, or lines (not shown) connecting the first disk 161 to the second disk 162, or comparable structure to limit the distance the first disk 161 slides along the delivery device 20 during systole. In an alternative version of the embodiment of FIG. 4D, the first disk is attached at the center to the second disk, e.g., around the catheter, so that the first disk may flex during the systolic phase to allow blood to flow through the inner radial portion of the second disk. The embodiment of FIG. 4D may be positioned in the blood vessel similarly to the embodiment of FIGS. 4A and 4B. The size of the inner radial portion 162*a* is as large as the smallest radius required to permit blood flow through the vessel. The remainder of the second disk 162, i.e., the outer radial portion 162*b*, is flexible as to sizing, so as to allow the filter portion of the valve-filter device, i.e., the second disk 162 to fit in the blood vessel. It is well within the skill in the art to determine the appropriate percent cross-sectional area for a particular application.

Suitable materials for the first and second disks of the embodiment of FIGS. 4A-4D are as discussed above for other embodiments of the invention. The inner and outer radial portions 162*a*, 162*b* of the second disk 162 could be made of the same material (with the inner portion made permeable by mechanical or chemical means) or they may be made of different materials.

In any of these aspects of the embodiment of FIGS. 4A-4D, the valve-filter device has a delivery configuration, in which the first (valve) disk 61, 161 and second (filter) disk 62, 162 are folded or wrapped around the delivery device 20.

In any of the above embodiments, the valve-filter device may be self-expandable. For example, in the embodiment of FIG. 4A-4D, the second disk may be self-expandable. The ring 142 and wires 144 of the embodiment of FIG. 2 control the diameter of the valve unit, which is also capable of reducing to near zero diameter. Alternatively, the valve and filter units or single unit valve-filter unit may be manually opened.

Figure 5B:
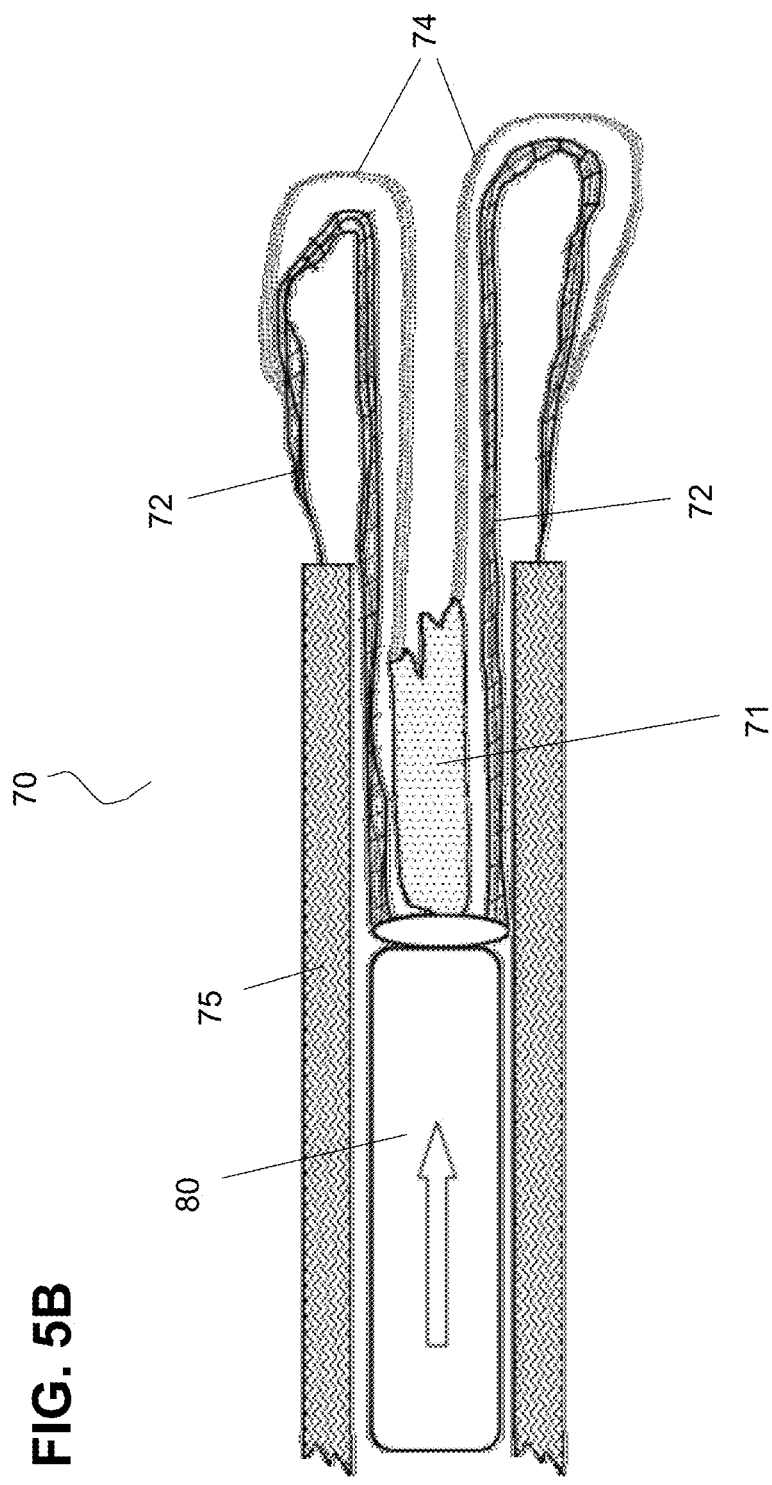
Figure 5C:
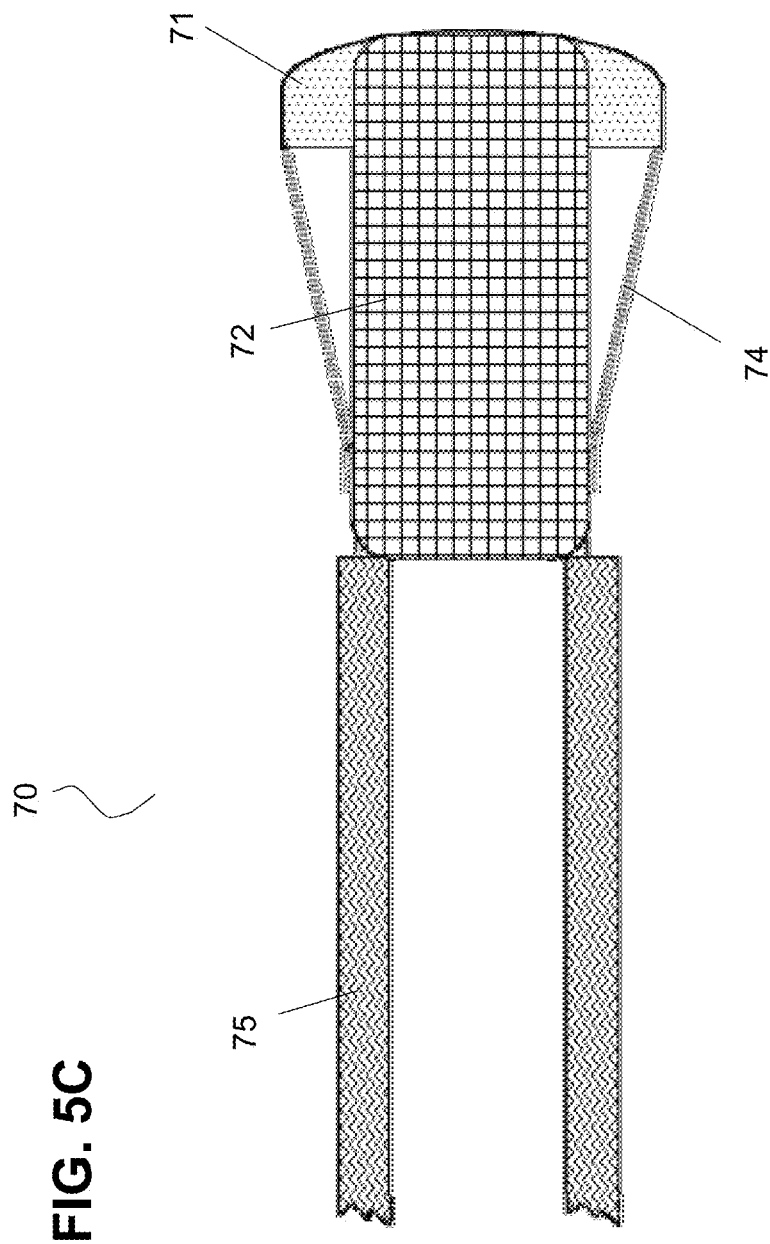

A percutaneous temporary valve system 70 and a method of deploying the temporary valve according to the invention is illustrated in FIGS. 5A-C. The temporary valve system includes a temporary valve 71, central core 72, a plurality of lines 74, a sheath 75, and a pusher 80. The central core 72 is tubular with an open proximal end, for example with a cuff to provide a pushing surface for the pusher 80, and an open distal end facing (adjacent or non-adjacent) or attached to the valve 71. The valve 71 has an open center region large enough to accommodate a delivery device passing therethrough, and the edge of the valve 71 open center region may be attached to the distal end of the central core 72, or it may have a diameter and stiffness sufficient to allow the distal end of the central core 72 to support and maintain the position of the valve center during systole. The plurality of lines 74 connect the rim of the temporary valve 71 to the central core 72. Each of the plurality of lines 74 may be attached to the central core 72 by means known in the art, for example, gluing or bonding. The lines 74 may be attached to the valve 71 by similar means. Preferably, the lines 74 are made of the same material as the valve 71. More preferably, the valve 71 and lines 74 are a unitary structure, constructed from a single mold with a polymer that includes the entire valve and lines, requiring no attachment.

The temporary valve system 70 has a delivery configuration, in which the valve 71 and central core 72 are inverted, for example folded back on itself like a folded sock (with an open toe), and housed within the sheath 75, along with the lines 74, as shown in FIG. 5A. The central core 72 is preferably in direct continuity with the pusher 80, and is made of a material that is sufficiently flexible to allow it to invert on itself and into the sheath 75 when folded. Preferably the pusher 80 has an outer diameter that matches the inner diameter of the sheath 75 so that it can push the components contained within the sheath 75 out of the sheath.

The temporary valve 71 will begin to function once the central core 72 and the temporary valve 71 have been pushed out of the sheath 75. The central core 72 preferably has a diameter large enough to accommodate a catheter carrying a permanent valve device or valve repair tool to pass through to deliver the permanent valve or repair tool to a site distal of the valve (and filter where used). Thus, in use, the delivery catheter may be inserted through the sheath and out the open distal end of the central core 72 and through the temporary valve (and filter where used).

In the embodiment of FIGS. 5A-C, the valve 71 of the temporary valve system has a jellyfish-like shape in its fully deployed configuration with a plurality of lines 74 that connect the rim of the valve 71 to the central core 72, for example near the proximal end of the central core 72, as illustrated in FIG. 5C. Alternatively, the lines 74 may be attached to the sheath 75 (not shown). In this embodiment, the lines and valve are manufactured as a single piece, for example by molding polymer material. Alternatively, the lines 74 may be wires or strings attached to the valve 71, the wires or strings may be made of the same material as the valve 71. The lines 74 provide tension during diastole to control the diameter of the valve 71. The lines 74 may be pulled forward or backward to control the diameter of the valve.

As illustrated in FIG. 5B, the valve 71 and central core 72 may be deployed by everting the valve and central core using a pusher 80. The pusher 80 may be, for example, a catheter. Each of the plurality of lines 74 are attached at a first end to the rim of the valve 71 and at a second end to a position on the central core 72, for example near the distal end 72b of the central core—distal end 72b of the central core 72 being the end furthest from the canopy of the temporary valve and the proximal end 72a of the central core 72 being attached to the canopy of the temporary valve 71. FIG. 5C illustrates a fully deployed temporary valve, with the central core extending down the center of the device. The temporary valve system of FIGS. 5A-5C may be used with any of the filter units described above, as illustrated in FIG. 6.

In one embodiment, the temporary valve of FIGS. 5A-5C is deployed proximal of the left subclavian artery (see, e.g., element 14 of FIG. 1). In embodiments such as FIG. 6, the filter unit is preferably deployed between the right brachial artery and sino-tubular junction (e.g., elements 12 and 11 of FIG. 1) to maximize trapping of emboli. The temporary valve of the embodiment of FIG. 6 may be deployed near the filter unit or more proximally, for example proximal of the left subclavian artery (see element 14 of FIG. 1). In embodiments where the temporary valve and filter unit are non-adjacent, the filter unit may be delivered and deployed using the delivery device used to deliver a permanent percutaneous valve device or valve repair tools.

Figure 6:
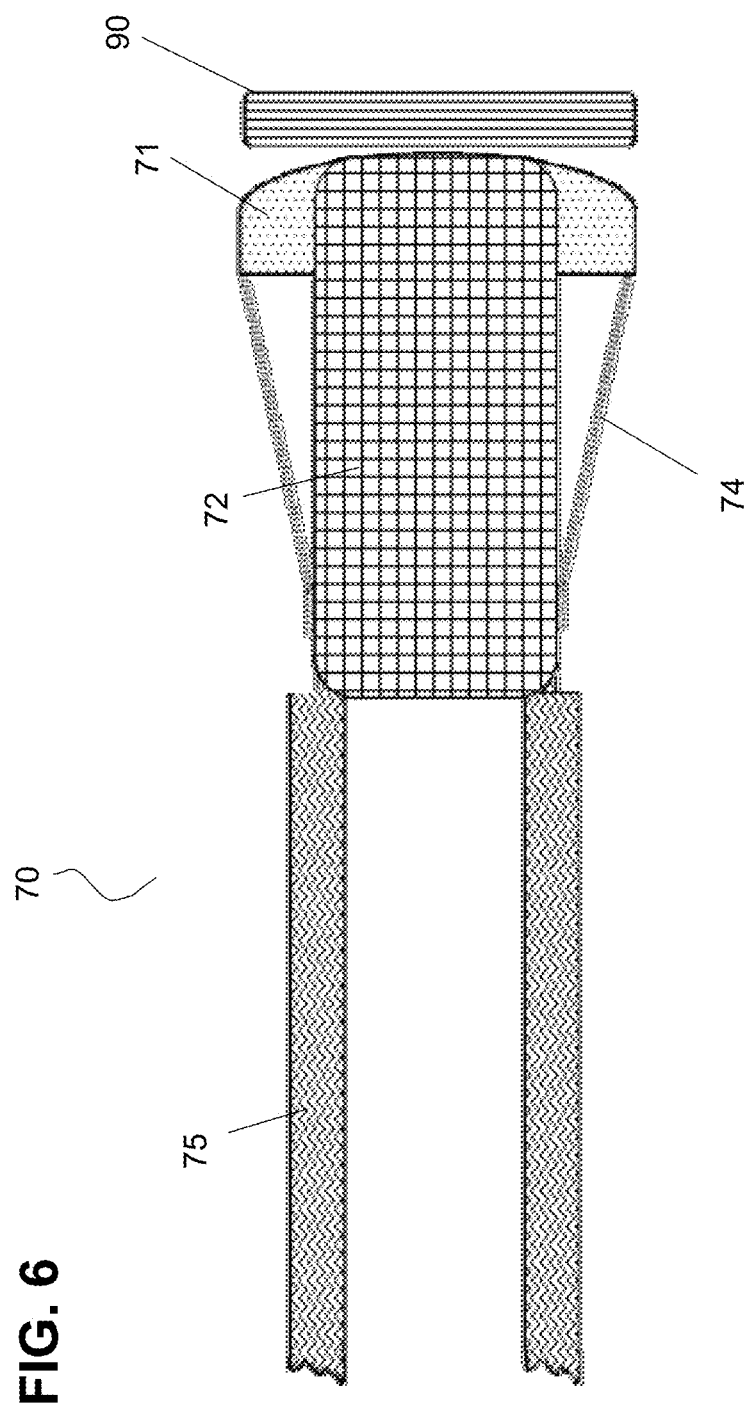
FIG. 6 illustrates the percutaneous temporary valve of FIGS. 5A-C fully deployed with an optional filter unit in a cut-away view.

The central core 72, which is the backbone of the temporary valve, may be made of a flexible material, such as a braid or mesh. The central core 72 may be made of a biocompatible metal, such as for example Nitinol or other shape memory material, or it may be made of a biocompatible fabric, such as for example a polymeric material. Non-limiting examples of polymeric materials include, for example, polyesters, such as Dacron and polyethylene terephthalate (PET), polytetrafluoroethylene (PTFE), polyurethanes, and nylon. The central core 72 may be constrained by the sheath 75 (or, as shown in FIG. 6 where an optional filter unit is adjacent the valve body—the delivery device 175) and the eversion of the central core 72 may take place by unconstraining the central core—pushing it out of the sheath, and allowing it to self-assemble. The valve 71 is attached to the central core 72 by a plurality of lines 74, and may also be attached at its apex—at the proximal end. For purposes of the temporary valve embodiment of FIGS. 5A-C and 6, "proximal" refers to the end of the component oriented closer to the heart if the device is deployed in the aorta and "distal" refers to the end of the component oriented away from the heart if the device is deployed in the aorta. Use of the temporary valve system of the invention where the central core 72 is tubular with an open end permits placement of the temporary valve anywhere, for example, along the aortic arch and percutaneously passing a second delivery device through the temporary valve to the native valve where the user may proceed with percutaneous valve replacement or valve repair.

The temporary valve system 70 may be used with or without a filter unit 90. Filter unit 90 may have an umbrella-shaped canopy, as described in FIG. 2 (filter unit 150), or may be substantially flat, as described in FIGS. 4A-C (filter unit 62).

Suitable materials for the temporary valve-filter device and temporary valve of the invention include fabrics, polymers, and tissue or other suitable biocompatible materials known in the art. Fabrics may include, e.g., PET, PTFE, ePTFE, polypropylene, and like materials. Polymers may include, e.g., PEBAX, silicone polycarbonate urethane, silicone, polyurethane, nylon, PET. Tissues may include bovine pericardium, porcine pericardium, or similar minimally immunogenic tissues.

The percutaneous temporary valve-filter system of the present invention may further comprise a permanent prosthetic device, such as a replacement valve device, or a repair tool for the repair of calcified valve. The permanent device or repair tool may be delivered using a different, i.e., second, catheter having a diameter smaller than the diameter of catheter 20, the first catheter, shown FIGS. 1, 2, 3, 4A, and 4B that permits it to pass through the catheter 20 to deliver the permanent device or repair tool to a site distal of the target site of the valve-filter or valve.

The present invention also relates to a method of deploying a temporary valve-filter device, for example to a target site of a blood vessel. The valve-filter device may be compressed and folded into a delivery configuration, leaving a reduced cross sectional profile, and housed in a catheter during the navigation in the artery. The valve-filter device may be released from the catheter, for example, by push rods and/or pull wires that are commonly used in percutaneous procedures, for example, upon reaching the target site in the blood vessel. After being released, the valve-filter device expands into its working configuration. For the single unit embodiment depicted in FIG. 1, in one aspect of the invention ring 33 may expand into a circle to contact the aorta wall 16 while the material of canopy 31 renders the valve-filter into an open umbrella shape. Push rods and pull wires may also be used to help maintain the open umbrella shape of the valve-filter. For the multi-unit embodiments depicted in FIGS. 2, 2A and 3, ring 33, 153 and 253 may similarly expand so that the rim of the filter unit 150, 250 presses against the aorta wall 16 effectively sealing the vessel against the passage of emboli. The plurality of struts 145, 245 may open radially by a self-expansion mechanism during deployment, such as through the hinges 146 depicted in FIG. 2A, or through expansion to a pre-set, for example thermo-mechanically pre-set curved shape as is depicted in FIG. 3, thereby transforming the valve unit 140, 140a, 240 into a working configuration. After the valve-filter device 130, 230 is deployed into a working configuration, a second delivery device having a smaller diameter may be threaded through the delivery device and extended past the valve-filter device to the site of permanent valve placement or valve repair. The device of FIGS. 4A-4D may be deployed in a similar manner.

In one embodiment, the temporary valve-filter system may further comprise a permanent percutaneous prosthetic valve, and the method may include deploying the permanent prosthetic device using the second delivery device, for example, an inner catheter, after deploying the temporary valve-filter. In another embodiment, the system may further include a valve repair tool, and the method includes deploying the repair tool from the second delivery device and repairing a native valve after deploying the temporary valve-filter.

The present invention also relates to a method of deploying a temporary valve. As described above for FIGS. 5A-5C, the method comprises providing a sheath containing a folded central core and temporary valve comprising a body and a plurality of lines, wherein said plurality of lines connects a peripheral rim of said temporary valve to said central core, and said central core is attached to the sheath; and pushing said folded central core and temporary valve from the sheath using a pusher, thereby everting the central core and temporary valve into a deployed configuration. Alternatively the lines may be attached to the sheath.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A percutaneous temporary valve system for use in percutaneous cardiovascular procedures, comprising a temporary valve having a central core, and a sheath for containing and delivering said temporary valve and said central core; said temporary valve comprising a valve body and a plurality of lines, each line of said plurality of lines connected at a first end to a rim of said valve body and at a second end to said central core; said central core having an inverted delivery configuration and connected to said sheath.

2. The system of claim 1, further comprising a pusher.

3. The system of claim 1 or 2, wherein said central core includes a pushing surface.

4. The system of claim 1, wherein each of said temporary valve and said central core has an open center region.

5. The system of claim 1, wherein said sheath includes a filter unit.

6. The system of claim 1, wherein said temporary valve comprises a valve structure impermeable to blood and a filter structure permeable to blood but impermeable to emboli, said temporary valve designed for simultaneously regulating flow of blood and collecting emboli.

7. The system according to claim 6, wherein said valve structure and said filter structure are separate units.

8. The system according to claim 1, wherein said temporary valve has an inverted delivery configuration.

9. The system of claim 8, wherein said temporary valve has an umbrella-shaped canopy.

10. A method of deploying a temporary valve comprising:
providing a sheath containing a temporary valve having a central core, said temporary valve comprising a valve body and plurality of lines, wherein said plurality of lines connects a peripheral rim of said valve body to said central core, and said central core has a folded delivery configuration forming a folded central core wherein said folded central core is inverted within said sheath and connected to said sheath;
pushing said folded central core and said temporary valve from said sheath using a pusher, while said sheath remains static; and
everting said central core into a deployed configuration, said temporary valve thereby assuming a deployed configuration.

11. The method of claim 10, wherein said central core comprises a shape memory material and said sheath constrains said central core in said delivery configuration.

12. The method of claim 10, wherein said sheath further contains a filter unit, said method including pushing said filter unit from said sheath to a deployed configuration, said filter unit located adjacent said valve body.

13. A percutaneous temporary valve-filter device for use in percutaneous cardiovascular procedures, comprising a valve structure impermeable to blood and a filter structure permeable to blood but impermeable to emboli, said valve-filter device designed for simultaneously regulating flow of blood and collecting emboli, said valve structure comprising a temporary valve having a central core, and a sheath for containing, delivering, and housing said temporary valve and said central core, said temporary valve comprising a valve body and a plurality of lines, each line of said plurality of lines connected at a first end to a rim of said valve body and at a second end to said central core; said central core having an inverted delivery configuration and connected to said sheath.

14. The device according to claim 13, wherein said filter structure comprises a substantially flat portion.

15. The device according to claim 13, wherein said filter structure comprises an umbrella-shaped canopy; said umbrella-shaped canopy having an apex, a base, an open shape in a deployed working configuration, and a closed shape in a delivery configuration, said base comprising a rim, said umbrella-shaped canopy having a convex surface and a concave surface in said deployed working configuration.

16. The device according to claim 13, wherein said filter structure has a porosity in a range of 10-2000 µm diameter.

17. The device according to claim 13, wherein said porosity is in a range of 50-500 µm diameter.

18. The device according to claim 13, wherein said porosity is in a range of 80-200 µm diameter.

19. A system comprising the valve-filter device of any one of claims 12, 13, 14, 15, 16, and 17 and a first delivery device, said valve-filter device mounted in said first delivery device.

20. The system according to claim 19, further comprising a second delivery device and a percutaneous valve device for implantation in a blood vessel.

21. The system according to claim 20, wherein said first delivery device has a lumen having an internal diameter sufficiently large for said second delivery device to pass therethrough.

22. The system according to claim 20, further comprising a valve repair tool for repairing a native valve.

23. The device according to claim 13, wherein said temporary valve has an inverted delivery configuration.

24. The device according to claim 23, wherein said temporary valve has an umbrella-shaped canopy.

25. The device according to claim 13, wherein said valve structure and said filter structure are separate units.

26. A method of deploying a temporary percutaneous valve-filter device for use in percutaneous cardiovascular procedures, comprising:
introducing into a vessel, a system comprising:
a valve-filter device mounted on a first delivery device having a lumen, said valve-filter device having a radially collapsed delivery configuration, said valve-filter device comprising: a temporary valve having a central core, and said first delivery device for containing and delivering said temporary valve and said central core, said temporary valve comprising a valve body and a plurality of lines, each line of said plurality of lines connected at a first end to a rim of said valve body and at a second end to said central core; said central core having an inverted delivery configuration and connected to said first delivery device;

advancing said valve-filter device to a target site;

deploying said valve-filter device from said first delivery device; and expanding radially said valve-filter device to a working configuration designed for simultaneously regulating flow of blood and collecting emboli.

27. The method of claim 26, wherein said system further comprises a second delivery device and a percutaneous valve device for implantation, said lumen of said first delivery device having an internal diameter sufficiently large for said second delivery device to pass therethrough, said method further comprising after said expanding:

extending said second delivery device through said first delivery device;

deploying and implanting said percutaneous valve device; and retracting said second delivery device.

28. The method of claim 26, wherein said system further comprises a second delivery device and a percutaneous valve repair tool, said lumen of said first delivery device having an internal diameter sufficiently large for said second delivery device to pass therethrough, said method further comprising after said expanding:

extending said second delivery device through said first delivery device;

deploying said valve repair tool and repairing a native valve;

retracting said repair tool; and retracting said second delivery device.

* * * * *